United States Patent [19]
Maruyama et al.

[11] Patent Number: 5,487,741
[45] Date of Patent: Jan. 30, 1996

[54] BONE PLATE

[75] Inventors: Yu Maruyama; Yoshu Taguchi, both of Tokyo; Kijuro Hayano, Chino, all of Japan

[73] Assignee: Taguchi Medical Co., Ltd., Tokyo, Japan

[21] Appl. No.: 152,426

[22] Filed: Nov. 12, 1993

[30] Foreign Application Priority Data

Nov. 16, 1992 [JP] Japan ................. 4-084967 U

[51] Int. Cl.⁶ .................. A61B 17/56; A61B 17/58; A61F 2/30; A61F 2/28
[52] U.S. Cl. ................. 606/60; 606/69; 606/71; 623/16
[58] Field of Search ............... 623/16; 606/59, 606/60, 69, 70, 71, 72, 86, 101; 602/9, 32

[56] References Cited

U.S. PATENT DOCUMENTS

| 2,825,329 | 3/1958 | Caeser | 606/71 |
| 4,629,463 | 12/1986 | Grundei et al. | 623/16 |
| 4,651,724 | 3/1987 | Berentey et al. | 606/69 |
| 4,988,351 | 1/1991 | Paulos et al. | 606/75 |
| 5,133,718 | 7/1992 | Mao | 606/60 X |

FOREIGN PATENT DOCUMENTS

| 1112803 | 11/1981 | Canada | 606/70 |
| 2435243 | 5/1980 | France | 606/69 |
| 549079 | 4/1932 | Germany | 606/69 |
| 1502020 | 8/1989 | U.S.S.R. | 606/69 |

Primary Examiner—David Isabella
Assistant Examiner—Laura Fossum
Attorney, Agent, or Firm—Dorn, McEachran, Jambor & Keating

[57] ABSTRACT

A bone plate adapted to be attached to the surface of a bone across the broken-away portion of the bone to thereby fix the broken-away portion is provided with a body provided with a bottom surface formed so as to contact with the bone and a surface formed so as not to impart trouble to an upper tissue, and formed so as to extend in one or more directions, at least one opening formed in the body for receiving a fastener therein and fixing the bone plate, and a pin formed so as to protrude from the bottom surface of the body, and formed so as to be able to be driven into the bone to thereby at least tentatively set the body relative to the bone.

13 Claims, 3 Drawing Sheets

BONE PLATE

BACKGROUND OF THE INVENTION

1. Field of the Invention

This invention relates to a bone joiner which is adapted to be attached to the surface of a bone across of the broken-away portion of the bone by means of screws or the like and is used to fix the broken-away portion, and particularly to a small bone plate suitable for joining cranial bones and facial bones.

2. Related Background Art

Bone plates formed with a plurality of fixing holes for inserting embedded screws into an elongated plate-like or ladder type body have heretofore been used as bone plates for fixing the broken-away portion of a bone such as the fractured portion of a bone or the excised portion of a bone in a coordinated state. These are generally formed of an inert material such as stainless steel, pure titanium or a titanium alloy, and are embedded in the human body for a long time or permanently. For the attachment of the bone plate, the bone plate is first positioned on the surface of a bone so as to stride over the broken-away line with the broken-away portion coordinated, and the positions of screw holes for embedding screws therein are determined. Screw holes are then formed at determined locations on the surface of the bone. Finally, the bone plate is again positioned on the surface of the bone, the embedded screws are inserted into the fixing holes and threadably inserted into the screw holes, and the bone plate is fixed to the bone.

Such bone plates of the prior art include relatively large bone plates used for fractured thighbornes or the like and small bone plates used for fractured facial bones, cranial bones, etc. They are, for example, Japanese Patent Application Laid-Open No. 53-146487, Japanese Patent Application Laid-Open No. 57-081333, Japanese Patent Application Laid-Open No. 63-186642, Japanese Patent Application Laid-Open No. 63-270044, Japanese Patent Application Laid-Open No. 1-190348, Japanese Utility Model Application Laid-Open No. 2-094515, Japanese Patent Application Laid-Open No. 2-503877, Japanese Patent Application Laid-Open No. 3-503020, etc. Of these, Japanese Patent Application Laid-Open No. 63-270044 includes a description of a microplate set particularly matching the three-dimensional shapes of the face and head. These publications include several proposals about the shapes of bone plates sufficiently fit for the surfaces of bones for inserting therein screws to be inserted into bones, in order to fix fractured bone portions reliably.

In these bone plates, however, it can be said that no sufficient measures are adopted for the operability when the bone plate is fixed to a fractured bone portion. For example, it is necessary to apply the bone plate to a fractured bone portion in advance and confirm the attachment position, and then form a mark or the like on the surface of the bone, and once remove the bone plate and form screw holes at locations on the surface of the bone which correspond to the fixing holes in the bone plate, and thereafter apply the bone plate again to the fractured bone portion and fasten it by screws. That is, according to the above-described prior-art bone joiner, it is difficult to position the bone joiner while holding the fractured bone portion in its coordinated state by one alone and moreover, it is necessary to determine the locations of the screw holes, and the working property thereof has been very inferior.

Particularly the microplate described in Japanese Patent Application Laid-Open No. 63-270044 is in itself so small that it makes one feel difficult to grasp it and therefore, requires a great effort in fitting the plate to an optimum location on a fractured bone portion. That is, in the case of a joining operation on the head and portions around it, such as cranial bones, the nasal bone and the jawbone, both of the fractured bone portion and the bone joiner are small and these are regions of the body which are difficult to support the bones and therefore, it is impossible to work quickly and appropriately.

On the other hand, Japanese Patent Application Laid-Open No. 3-057446 (U.S. Pat. No. 4,923,471) and U.S. Pat. No. 4,959,065 disclose a bone plate having a handle for gripping attached to the marginal edge portion thereof, and adapted to be positioned or fastened with the handle gripped in the work of fixing a fractured bone portion, the handle being removed after the fastening of the bone plate is completed. In this case, the work of positioning the bone plate and the work of fastening the bone plate become easy because of the presence of the handle. However, the work of forming screw holes must be done after the bone plate has once been removed, and during the work, the bone itself must be supported by other method (for example, a helper or other fixing tool). Also, such handle has its connected portion to the bone plate formed into a narrow neck and is adapted to be torn off after the bone plate is fixed to the fractured bone portion, but burrs may remain on the bone plate after the handle is torn off, they may injure the tissue around the fractured bone portion.

SUMMARY OF THE INVENTION

It is an object of the present invention to provide a bone plate which is improved in the working property during actual bonesetting, and particularly the handleability in the positioning and fixing work.

It is another object of the present invention to provide a bone plate which enable the positioning and fixing work to be done quickly and accurately.

More specifically, it is an object of the present invention to provide a bone plate which can be tentatively set by driving a pin into a bone to thereby enable the positioning work to be easily done and which also enables the correction of the position to be simply accomplished.

It is another specific object of the present invention to provide a bone plate which, in the positioning when fractured or excised cranial bones are to be joined together, can eliminate the danger of the separated portions of the cranial bones coming off the bone joiner and enables the bonesetting work to be done without anxiety.

It is still another specific object of the present invention to provide a bone plate which facilitates positioning and supporting by a grip member and leaves no burr on the surface of the body of the bone plate after the grip member is removed.

The bone plate of the present invention includes a body provided with a bottom surface formed so as to contact with a bone and a surface formed so as not impart trouble to an upper tissue, and formed so as to extend in one or more directions, at least one opening formed in the body for receiving a fastener therein and fixing the bone plate, and a pin formed so as to protrude from the bottom surface of the body and formed so as to be able to be driven into the bone to thereby at least tentatively set the body relative to the bone.

Also, the bone plate of the present invention includes a body provided with a bottom surface formed so as to contact with a bone and a surface formed so as not to impart trouble to an upper tissue, and formed so as to extend in one or more directions, a bend bent in the other portion than the end portions of the body in a direction having an angle with respect to the bottom surface of the body, and a pair of mount portions extending on the opposite sides of the bend and formed so as to extend substantially in parallelism to each other, the bottom surfaces of the pair of mount portions being formed reversely to each other, each of the mount portions being provided with fastening means for fixing itself to the surface of the bone.

Further, the bone plate of the present invention includes a body provided with a bottom surface formed so as to contact with a bone and a surface formed so as not to impart trouble to an upper tissue, and formed so as to extend in one or more directions, fastening means formed at least two mutually spaced apart locations on the body, and a separable grip member inserted in the marginal edge portion of the body and connected to said body in such a manner as to hold the marginal edge portion.

DESCRIPTION OF THE PREFERRED EMBODIMENTS

Figure 1:
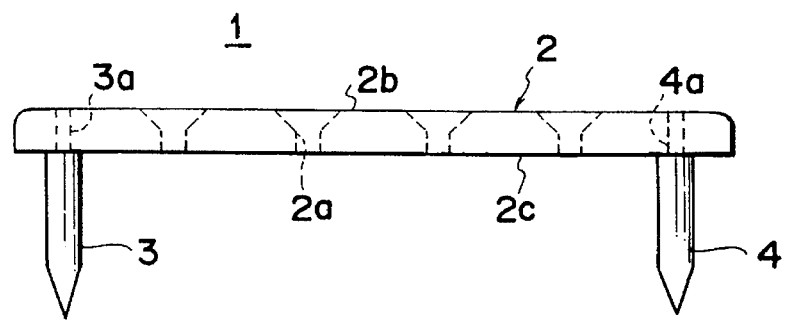
FIG. 1 is a side view showing the structure of a first embodiment of a bone joiner according to the present invention.
Figure 2:
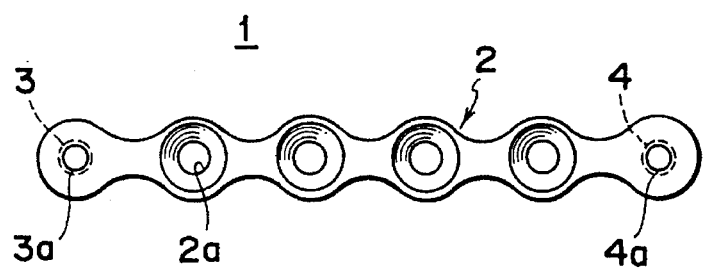
FIG. 2 is a plan view showing the structure of the first embodiment shown in FIG. 1.

FIGS. 1 and 2 show a first embodiment of a bone plate according to the present invention which is formed of a material such as pure titanium or a titanium alloy. This bone plate 1 comprises a straightly extending body 2 having fixing holes 2a formed at substantially equal intervals therein, and the upper portion of each fixing hole 2a is an upwardly enlarged, conical bore or counterbore portion which is adapted to bear against the head edge of an embedded screw, and the lower portion of each hole 2a is a straight bore portion. The surface 2b of the body 2 is formed into a smooth surface having no edge so as not to injure the tissue exterior of bones. The bottom surface 2c of the body 2 is a surface for contacting with a bone, and when this bone plate is applied, for example, to a thighbone, the bottom surface 2c is formed, for example, into a widthwisely curved surface correspondingly to the surface shape of the thighbone, and when the bone plate is applied to cranial bones, the bottom surface 2c is formed into a lengthwisely curved surface along the curved surface of the cranial bones.

On the opposite end portions of the body 2, there are provided pins 3 and 4 protruding from the bottom surface 2c thereof. The base portions 3a and 4a of these pins 3 and 4, respectively, are inserted in holes in the body and fixed to the body by welding. Basically the pins 3 and 4 may be provided only on one end portion of the body 2, and the shape thereof may be any shape if required strength is provided thereby and the pins can be driven into a bone. That is, the diameter of the pin is determined so that the pin is able to bear a force applied when the pin is driven into the bone, the length of the pin is determined so as to obtain a sufficient fixation of the bone plate to the bone, the angle of a pointed end of the pin is determined so as to facilitate the work of driving the pin into the bone.

The pins may be attached to any positions on the body, but when the working property for positioning is taken into account, it is desirable that the pins be formed on the end portions of the body 2.

In a joining operation using the above-described first embodiment, for example, the pin 3 is driven into the surface of one bone to be joined to such a degree that the pin will not come off, and then the coordinated state thereof with the other bone is adjusted and the position of the joiner is confirmed. If here, there is no problem in the position, the pin 3 is completely driven into the bone and fixed, and is coordinated with the other bone, whereafter the pin 4 is also driven into the other bone. Then, screw holes are formed from the surface of the bones and the bone plate is fixed by embedded screws as has heretofore been done.

If there is any problem in the mounted position of the bone plate with the bone plate once tentatively set by driving the pin 3 into the surface of the bone, the bone plate can be simply removed and the pin can be driven again into any other location. It is also possible to once remove the bone plate and then form screw holes in the bone, and in such case, if the pin 3 is driven again into the location into which the pin has once been driven and removed to leave its trace, after the screw holes are formed, the bone plate can be accurately mounted at the same location. Also during the fixing in which the embedded screws are threaded into the bone, the bone plate is fixed by the pin and therefore, the work can be done easily without the mislocation of the bone plate being feared.

In this embodiment, pins are provided on the opposite end portions of the body 2, but the above-described improved working property can also be obtained if a pin is provided only on one end portion of the body 2. In such case, however, the fractured bone portions cannot be held in their coordinated state by driving the pin into the bone. The length, diameter, cross-sectional shape, etc. of the pin are not particularly restricted if the pin is one which can be driven into the bone, and should be suitably selected depending on the thickness and shape of the bone to be repaired. The bone plate of the present embodiment is provided as a microplate set for use for the bone joining of the jaw, face and cranial portions, and as the typical dimensions thereof, the length of the body 2 is 8 mm to 90 mm, the width of the body 2 is 0.8 mm to 4.5 mm, and the thickness of the body 2 is 0.5 mm to 1.5 mm. The fixing hole is formed with a conical bore portion having a maximum diameter of 1 mm to 4 mm so as to open toward the surface 2b of the body 2, and is connected to the straight bore portion of a diameter of 0.7 mm to 2.7 mm formed in the bottom surface of the body 2. Preferably, the diameter of the pin may of 0.5 mm to 1.2 mm, the length of the pin may be 1 mm to 5 mm, and the angle of the conical shape of the tip end of the pin may be 30° to 60°, and these are suitably changed depending on the region of bone to which the bone plate is applied.

Figure 3:
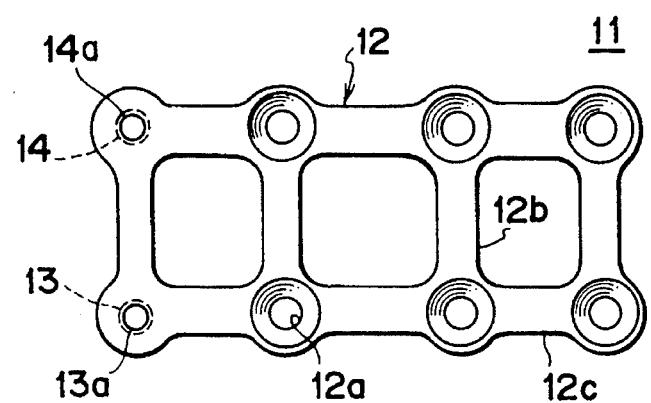
FIG. 3 is a plan view showing the structure of a second embodiment of the bone joiner according to the present invention.

FIG. 3 shows a second embodiment of the present invention. The body 12 of the bone plate 11 of this embodiment is generally of a ladder shape comprising laterally extending connecting plates 12b and longitudinally extending connecting plates 12c. A fixing hole 12a is formed in each of the portions of intersection of this ladder-shaped bone plate, and in the endmost portion of intersection, pins 13 and 14 similar to the pins 3 and 4 in the first embodiment are attached to the bottom surface so as to protrude under the bottom surface, by their bases 13a and 14a being secured to the bone plate by welding.

Such a ladder-shaped bone plate can support a bone at a plurality of points in a plane and therefore is also used to repair a complicated fractured bone portion having a plurality of fracture lines. Besides such ladder shape, the plane shape of the bone plate may be a shape having arms extending in a plurality of directions, such as X-shape, Y-shape, T-shape, L-shape, I-shape or H-shape, a closed loop shape such as a triangle, a square or a circle, a checkerboard shape provided with fixing holes in the checkers thereof and having the checkers connected together lengthwisely and widthwisely, and one of these shapes is suitably selected for use depending on the situation of the broken-away portion of the bone or the broken-away region of the bone. The mounted positions of the pins should be suitably chosen in accordance with such a plane shape. The mounted positions of the pins are not restricted to the end portion of the body, but for example, when in a fractured bone portion, a plurality of separated fragments exist around the fixed central bone portion, it is necessary to stud pins in the plurality of end portions of the bone plate and attach a pin also to the vicinity of the central portion of the body.

Figure 4:
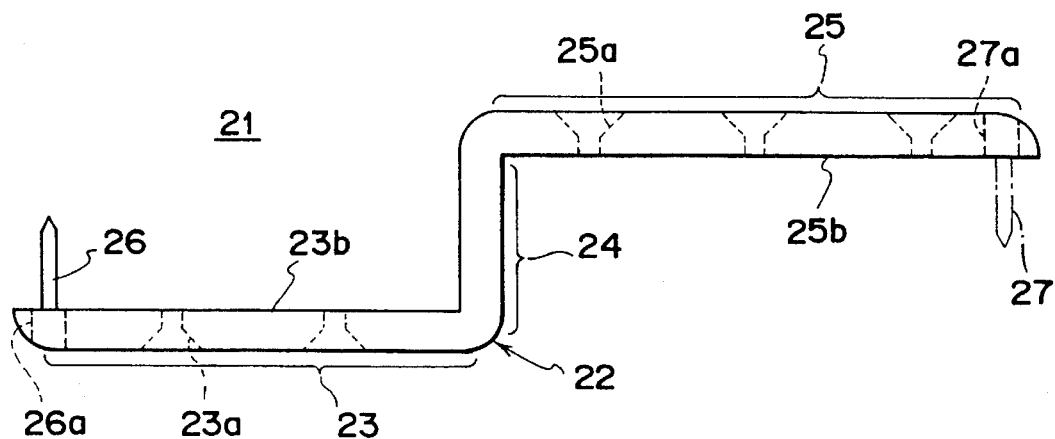
FIG. 4 is a side view showing the structure of a third embodiment of the bone joiner according to the present invention.

FIG. 4 shows a bone plate 21 which is a third embodiment of the present invention. In this embodiment, a body 22 is provided with a bend 24 at the center thereof, and mount portions 23 and 25 existing on the opposite sides of the bend 24 have bottom surfaces 23b and 25b formed so that their front surfaces are opposite to each other. Correspondingly to the formation of these bottom surfaces, fixing holes 23a and 25a have conical bore portions enlarged reversely to each other in the vertical direction, and pins 26 and 27 (in some cases, the pin 27 is not provided) are attached so as to protrude in vertically opposite directions. The mount portions 23 and 25 are basically formed so as to extend in parallelism to each other, but in some cases, they are generally curved or formed slightly non-parallel to each other, depending on the shape of the bone in the joined portion.

Figure 5:
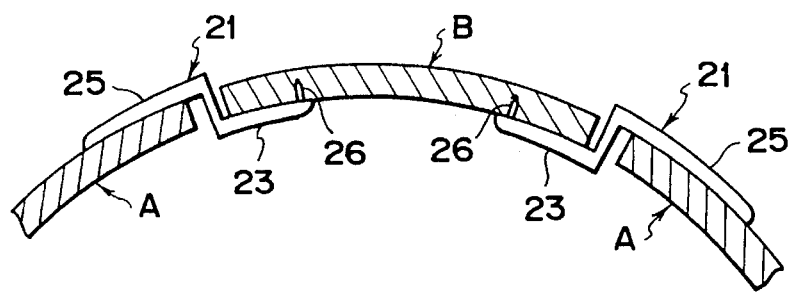
FIG. 5 is a cross-sectional view showing a state in which the third embodiment shown in FIG. 4 is used for the joining of cranial bones.

FIG. 5 illustrates a case where cranial bones are joined together by the use of the present embodiment. For example, a portion B of the cranial bones A is excised, whereafter the joining of this excised portion B is carried out in the following manner. With the excised portion B removed, the pin 26 of the bone plate 21 (in some cases, a plurality of bone plates are use as shown in FIG. 5) is first driven into the back of the excised portion B, whereby the bone plate is tentatively set. With the tentatively set bone plate 21, the excised portion B is then coordinated to the cranial bone, and as shown in FIG. 5, the mount portion 25 is brought into contact with the surface of the cranial bone A. In this state, whether the position of the bone plate 21 is adequate is examined while the position of the excised portion B is adjusted. If there is no problem here, the excised portion B is again taken out and screw holes are formed therein, and screws are threaded into the fixing holes 23a to thereby fix the bone plate, and the bone plate is again coordinated to the cranial bone, whereafter screw holes are formed also in the cranial bone A and screws are threaded into the fixing holes 25a to thereby fix the bone plate. If the position of the bone plate 21 is not good or when the bone plate 21 is to be temporarily removed for the formation of screw holes, work similar to that described above in connection with the first embodiment can be done.

This embodiment has, besides the effect of the above-described first embodiment, an advantage that when the bone plate is tentatively set by the pin, there is not the risk of the pin coming off during the work and the excised portion B falling into the interior of the cranial bones. Further, the pin 26 is driven from the back side of the excised portion B and the mount portion 23 supports the excised portion B from under it, and this also leads to the effect that an operation can be done without any psychological anxiety.

Also, on the basis of the bent shape of the body 22, the excised portion B is supported to the cranial bones A around it by the mount portion 25 and therefore, even if the hand is released during an operation, the bone plate will be maintained in the state shown in FIG. 5, and the working property is improved. This embodiment is a joiner particularly suitable for the permanent fixing of cranial bones, and can greatly mitigate the operator's physical and psychological burdens.

Figure 6:
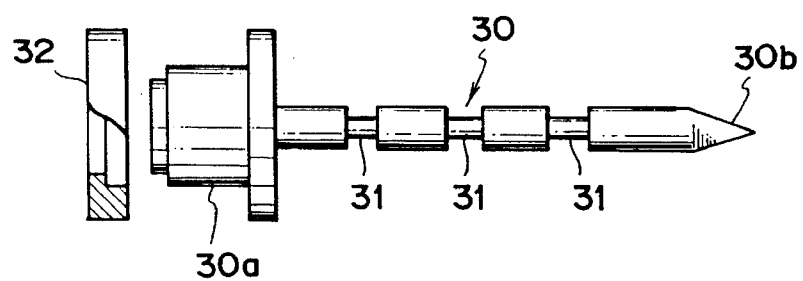
FIG. 6 is a side view showing another example of the pin adoptable in each embodiment.

FIG. 6 shows another example of the pin used in each of the above-described embodiments. This pin 30 is mounted by inserting a base 30a into a mounting hole formed in the body of the bone plate from the bottom surface side, fitting a fixing member 32 from the front surface side, and securing the two to each other as by welding. At this time, the pin 30 is rotatable about its axis relative to the body of the bone plate. Accordingly, the pin driven into the bone when the bone plate is tentatively set can be rotated without being moved and therefore, the positioning of the bone plate and the positioning of screw holes become very easy and also, the pin can be prevented from coming off the bone plate during the positioning work.

Also, this pin 30 is provided with a plurality of surface grooves 31 between the base 30a and a tip end 30b, and these surface grooves 31 do not hamper the driving work when the pin is driven into the bone, and after the pin is embedded in the bone, the bone eats into the grooves in accordance with the regeneration of the bone, whereby the bone plate is firmly fixed.

The above-described bone plate of the present invention is provided with fixing holes and pins as fastening elements to a bone, and the pins are used as fastening elements for tentative setting, and besides, may be provided for permanent fixing, instead of the fixing holes. For example, a fixing hole alone may be provided in one end portion of the bone plate and a pin alone may be provided in the other end portion of the bone plate.

Figure 7:
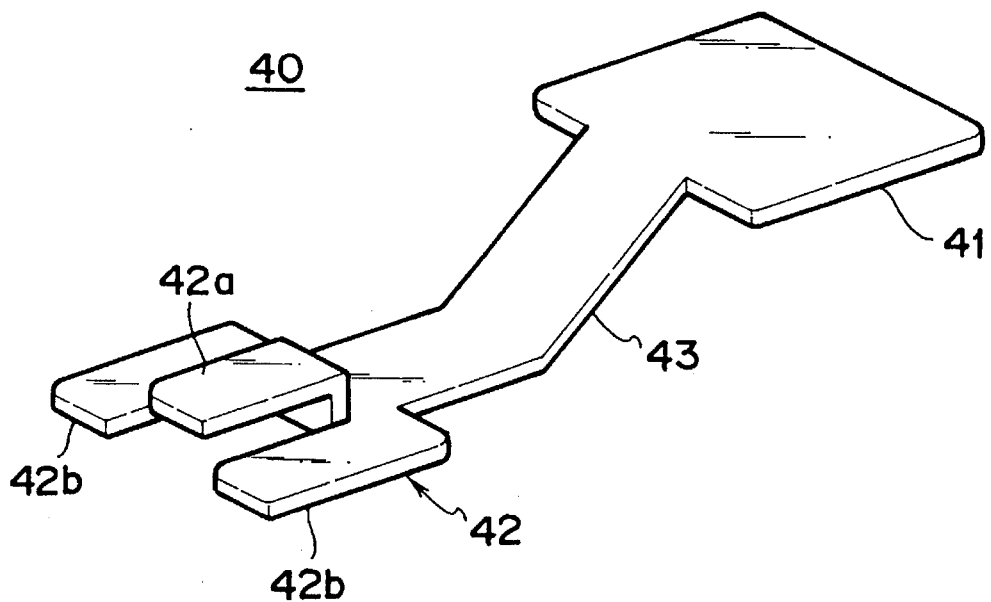
FIG. 7 is a perspective view showing the shape of an embodiment of a grip member according to the present invention.

FIG. 7 shows a grip member to be mounted on the bone plate according to the present invention. This grip member 40 comprises a plate-like grip portion 41 having a sufficient area to be gripped by fingers, a holding portion 42 for holding the marginal edge portion of the bone plate from above and below it, and a connecting portion 43 formed into a bent shape to dispose the grip portion 41 above the holding portion 42. The holding portion 42 has an upper jaw 42a for contacting with the upper surface of the bone plate, and a pair of lower jaws 42b for contacting with the bottom surface of the bone plate. The shape of this holding portion 42 is convenient for forming the grip member 40 by a plate and a gap is formed between the pair of lower jaws 42b, whereby the holding portion 42 can evade the pin protruding from the bottom surface of the marginal edge portion and can therefore be mounted at any position on the entire marginal edge of the bone plate. In case that a pair of upper jaws are formed as well as the lower jaws 42b, the holding portion can also evade the fixing hole formed in the marginal edge portion of the bone plate.

Figure 8:
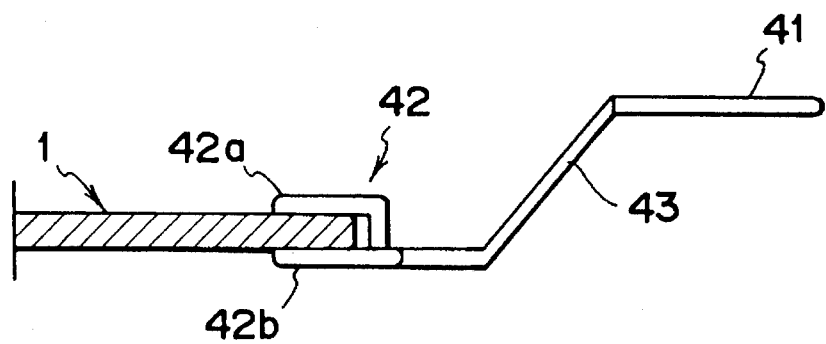
FIG. 8 is a view partly in cross-section showing a state in which the grip member shown in FIG. 7 is connected to a bone plate.

This grip member 40, as shown in FIG. 8, is mounted in such a manner that any marginal edge portion of the bone plate 1 is held between the upper jaw 42a and the lower jaws 42b. If the grip member 40 is made of a metal, the mounting of the grip member 40 to the bone plate 1 is effected by urging the upper jaw 42a and lower jaws 42b against the bone plate 1 in the state shown in FIG. 8. If for example, the grip member is formed of a plastic metal, the bone plate 1 having the grip member 40 mounted thereon is placed on a support bed, the grip member 40 is flat-pressed or punched from above the upper jaw 42a to thereby connect the grip member 40 to the bone plate. On the other hand, if the grip member is made of a resilient metal or a material of high elasticity such as resin, the spacing between the upper jaw 42a and the lower jaws 42b is set so that the bone plate may be held therebetween with appropriate pressure when the bone plate is inserted between the upper jaw 42a and the lower jaws 42b, whereby the pressing work or the like becomes unnecessary.

The grip member 40 connected to the bone plate 1 in this manner is utilized to position and fix the bone plate 1 during an operation. At a point of time whereat the grip member has become unnecessary, the grip portion 41 is moved up and down or to right and left, whereby the pressure contact state or the elastically connected state can be released to thereby remove the grip member 40. This grip member, after removed, leaves no bur on the bone plate and therefore, there is no possibility of injuring the surrounding tissue after an operation. Also, the location at which the grip member is connected to the bone plate may be arbitrarily set if on the marginal edge portion thereof, and after it has once been removed, the grip member can be re-connected to the same location or a different location.

What is claimed is:

1. A bone plate adapted to be attached to a surface of a bone across a broken-away portion of the bone to thereby fix the broken-away portion, said bone plate comprising:

a body including a bent portion between a pair of mount portions;

said mount portions having bottom surfaces adapted to contact the bone and upper surfaces adapted to be compatible with upper tissue, said mount portions extending from said bent portion to opposite ends of said body and being substantially parallel to each other, said bottom surfaces oppositely facing each other, said bent portion extending in a direction having an angle with respect to a plane of at least one of said bottom surfaces;

at least one opening formed in said body for receiving a fastener therein and fixing said bone plate; and at least one pin protruding from at least one of said bottom surfaces of said body, adapted to be driven into the bone to thereby at least tentatively set said body relative to the bone.

2. A bone plate according to claim 1, wherein said at least one pin is located on one of said opposite ends of said body.

3. A bone plate according to claim 1, wherein said at least one pin is formed with an annular surface groove.

4. A bone plate according to claim 1, wherein said at least one pin is rotatably attached to said body.

5. A bone plate according to claim 1, further a gripping member connected to said body which holds a marginal edge of said body.

6. A bone plate adapted to be attached to a surface of a bone across a broken-away portion of the bone to thereby fix the broken-away portion, said bone plate comprising:

a body including a bent portion and a pair of mount portions;

said mount portions having bottom surfaces adapted to contact the bone and upper surfaces adapted to be compatible with upper tissue, said mount portions extending from said bent portion to opposite ends of said body and being substantially parallel to each other, said bottom surfaces being positioned opposite each other in said mount portions, said bent portion extending in a direction having an angle with respect to at least one of said bottom surfaces; and fastening means provided on each of said mount portions for fixing said mount portions to said bone.

7. A bone plate according to claim 6, wherein at least one of said fastening means is an opening adapted to receive a fastener.

8. A bone plate according to claim 6, wherein each of said bottom surfaces of said mount portions is curved and thereby adapted to contact with a curved surface of a cranial bone.

9. A bone plate according to claim 6, wherein at least one of said fastening means is a pin protruding from at least one of said bottom surfaces of said body, adapted to be driven into the bone to thereby at least tentatively set said body relative to the bone.

10. A bone plate according to claim 9, wherein said pin is located on one of said opposite ends of said body.

11. A bone plate according to claim 9, wherein said pin is formed with an annular surface groove.

12. A bone plate according to claim 9, wherein said pin is rotatably attached to said body.

13. A bone plate system or kit according to claim 6, further comprising a grip member connected to said body which holds a marginal edge of said body.

* * * * *